(12) United States Patent
Trope (10) Patent No.: US 6,972,142 B2
(45) Date of Patent: Dec. 6, 2005

(54) CARD HAVING MULTIPLE LAYERS INDICATING RELATIVE HUMIDITY

(76) Inventor: Robert L. Trope, 399 150th Ave., #105A, Madeira Beach, FL (US) 33708

(*) Notice: Subject to any disclaimer, the term of this patent is extended or adjusted under 35 U.S.C. 154(b) by 0 days.

(21) Appl. No.: 10/392,117

(22) Filed: Mar. 19, 2003

(65) Prior Publication Data

US 2004/0185207 A1    Sep. 23, 2004

(51) Int. Cl.[7] .............................................. B32B 9/00
(52) U.S. Cl. ................... 428/40.1; 428/913; 73/29.02; 73/29.04; 73/73; 73/335.13
(58) Field of Search ............... 428/411.1, 43, 428/46, 40.1, 41.8, 42.2; D19/1; 283/117; 73/73, 29.04

(56) References Cited

U.S. PATENT DOCUMENTS

| | | | |
|---|---|---|---|
| 3,290,812 A | * | 12/1966 | Hunkins ..................... 40/107 |
| 4,580,360 A | | 4/1986 | Gribb |
| 5,458,282 A | * | 10/1995 | Martin ....................... 229/92.8 |
| 5,520,041 A | * | 5/1996 | Haswell ..................... 73/29.04 |
| 6,092,841 A | * | 7/2000 | Best et al. .................... 283/56 |
| 6,153,280 A | | 11/2000 | Uffmann |
| 6,228,451 B1 | * | 5/2001 | Boudouris et al. ......... 428/40.1 |
| 6,663,679 B1 | * | 12/2003 | Duncan ................... 73/335.01 |
| 6,698,378 B1 | * | 3/2004 | Dick et al. .................. 116/206 |
| 6,699,569 B2 | * | 3/2004 | Lipper ........................ 347/105 |

* cited by examiner

*Primary Examiner*—Rena Dye
*Assistant Examiner*—Camie S. Thompson
(74) *Attorney, Agent, or Firm*—Larson & Larson, PA; Herbert W. Larson (57) ABSTRACT

A multi-layered card having a thin, flexible, non-moisture absorbable, printable first layer, a first high tack adhesive second layer on a back side of the first layer joining the first layer to a front face of a third layer of a moisture absorbable card stock. A back side of the card stock covered with a second high tack pressure sensitive adhesive fourth layer joining the card stock to a front face of a flexible magnet sheet fifth layer.

17 Claims, 9 Drawing Sheets

CARD HAVING MULTIPLE LAYERS INDICATING RELATIVE HUMIDITY

This invention relates to advertising cards. More specifically, it refers to a multi-layered card having a thin, flexible, non-moisture absorbable material laminated layer over moisture absorbable card stock joined with a first adhesive layer and a flexible magnet sheet joined to the card stock with a second adhesive layer, the card used for determining relative humidity in ambient air.

BACKGROUND OF THE INVENTION

Advertising cards such as shown in U.S. Pat. No. 6,228,451 contain indicia for promoting various products. The front face is a blank having a corona or non-corona treated surface. The cards can be attached to a ferrous metal object by adhering a flexible magnet sheet to the back of the card or coating the back of the card with a low tack adhesive so that the card can be removed from a wood or plastic surface and repositioned as desired. Since an advertising card is commonly positioned within a home, it would be useful to create a dual purpose for the card in determining moisture levels in the home. Molds, dust mites, bacteria, viruses and other harmful microbes thrive when the relative humidity in a home exceeds fifty percent. The key to mold control is moisture control. If indoor humidity is kept low; i.e., between thirty and fifty percent relative humidity, mold control is achieved. It would be a great advantage to a homeowner to have a no additional cost method of determining relative humidity so that a dehumidifier can be turned on when humidity exceeds fifty percent. Such a no additional cost relative humidity indicating device is needed.

SUMMARY OF THE INVENTION

The present invention solves the need for determining home relative humidity levels by employing a modified advertising card usually obtained from advertisers at no cost to the consumer. The card of this invention has a thin, flexible, non-moisture absorbable material such as a silver foil printable with indicia as a front sheet. The front sheet back surface is attached with a high tack adhesive, either heat activated or pressure sensitive, to a six to ten point card stock that absorbs moisture. In one version, a rear surface of the card stock is attached with a high tack heat activated adhesive to a front face of a flexible magnet sheeting. A back side of the magnet sheeting retains a low tack adhesive covered by a carrier sheet prior to use. The magnet can be attached to a ferrous metal or other substances such as wood, plastic, aluminum and stone by use of the low tack adhesive.

A lower portion of the card has perforations above a gauge adapted to show low humidity, just right humidity or high humidity. The gauge is removed and held at a right angle to the card attached to a vertical surface. The amount of curl of the card's bottom edge determines the relative humidity in the ambient air. The gauge positioned under the curled portion interprets the curl in terms of relative humidity.

BRIEF DESCRIPTION OF THE DRAWINGS

The invention can be best understood by those having ordinary skill in the art by reference to the following detailed description when considered in conjunction with the accompanying drawings in which.

DETAILED DESCRIPTION OF THE INVENTION

Throughout the following detailed description, the same reference numerals refer to the same elements in all figures.

Figure 1:
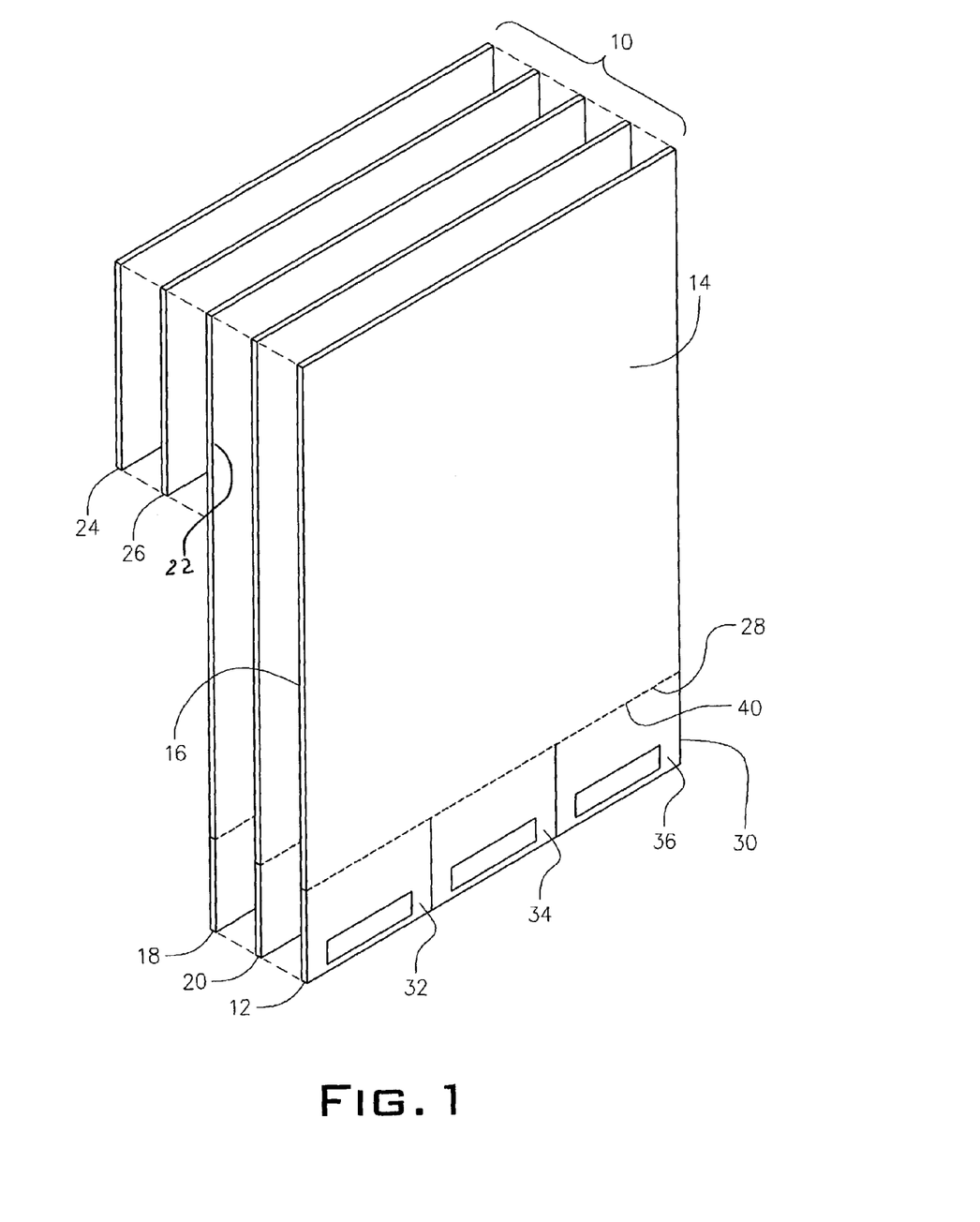
FIG. 1 is an exploded view of a five layered card of this invention.
Figure 2:
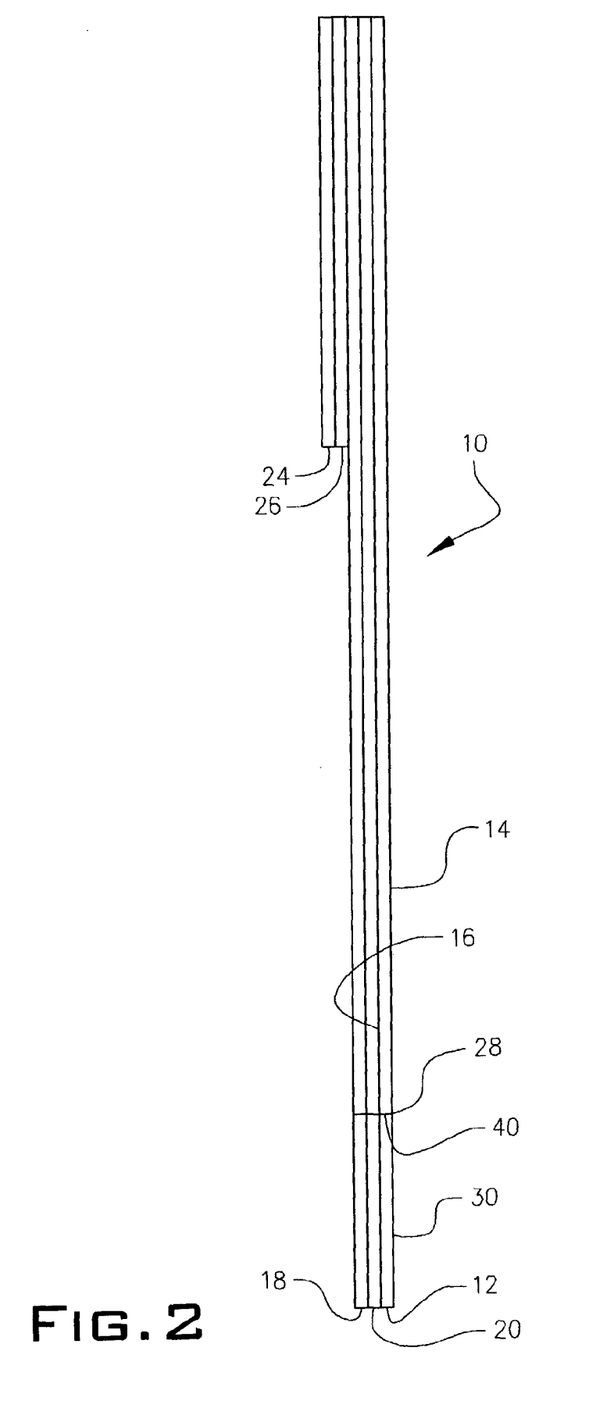
FIG. 2 is a side view of the five layered card of FIG. 1.
Figure 9:
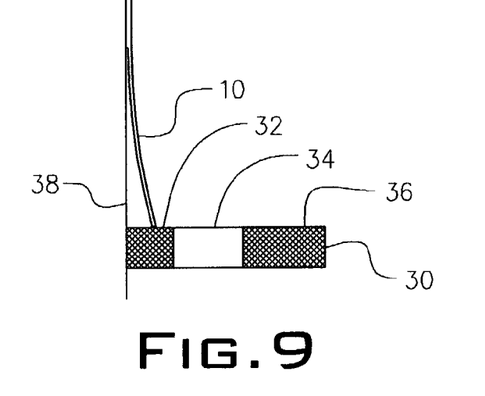
FIG. 9 is a side view of a card curled over a gauge showing low relative humidity.
Figure 10:
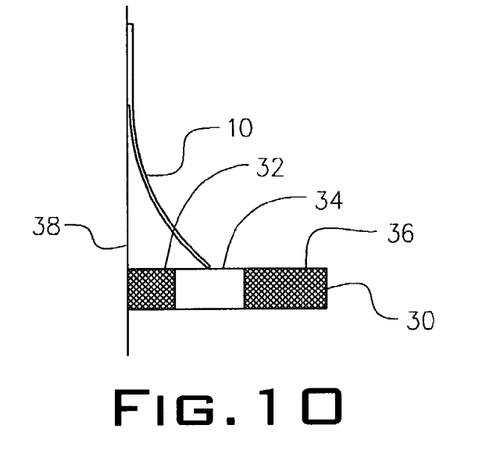
FIG. 10 is a side view of a card curled over a gauge showing relative humidity of thirty to fifty percent.
Figure 11:
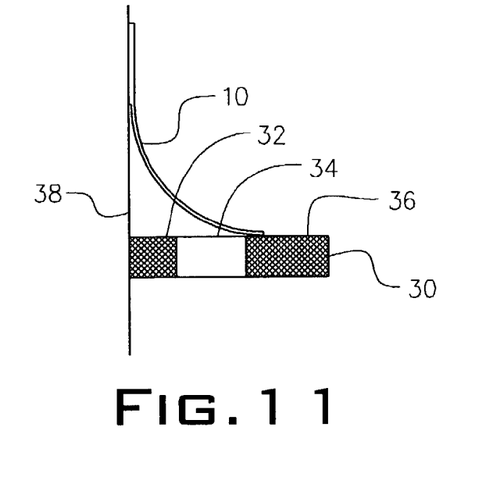
FIG. 11 is a side view of a card curled over a gauge showing a high relative humidity over fifty percent.

Referring to FIGS. 1–2, the card 10 has a first layer 12 of a printable, thin, flexible, non-moisture absorbable material such as polyvinyl chloride, polyester, cellophane or silver foil. A front surface 14 of first layer 12 contains indicia. A back surface 16 of first layer 12 is adhered to a six to ten point moisture absorbable card stock 18 by an intermediate high tack adhesive layer 20. A top portion 22 of the card stock 18 has a flexible magnet sheet 24 attached with a high tack adhesive 26. A lower portion of first layer 12 and the card stock 18 has a perforation line 28 for removal of a gauge 30. Referring to FIGS. 9–11, the gauge 30 has a low moisture indicating portion 32, a just right indicating portion 34 and a high humidity indicating portion 36. The gauge 30 is placed perpendicular to a vertical mounting surface 38 just below a bottom edge 40 of the card 10 to convert the degree of curl into a relative humidity reading.

Figure 3:
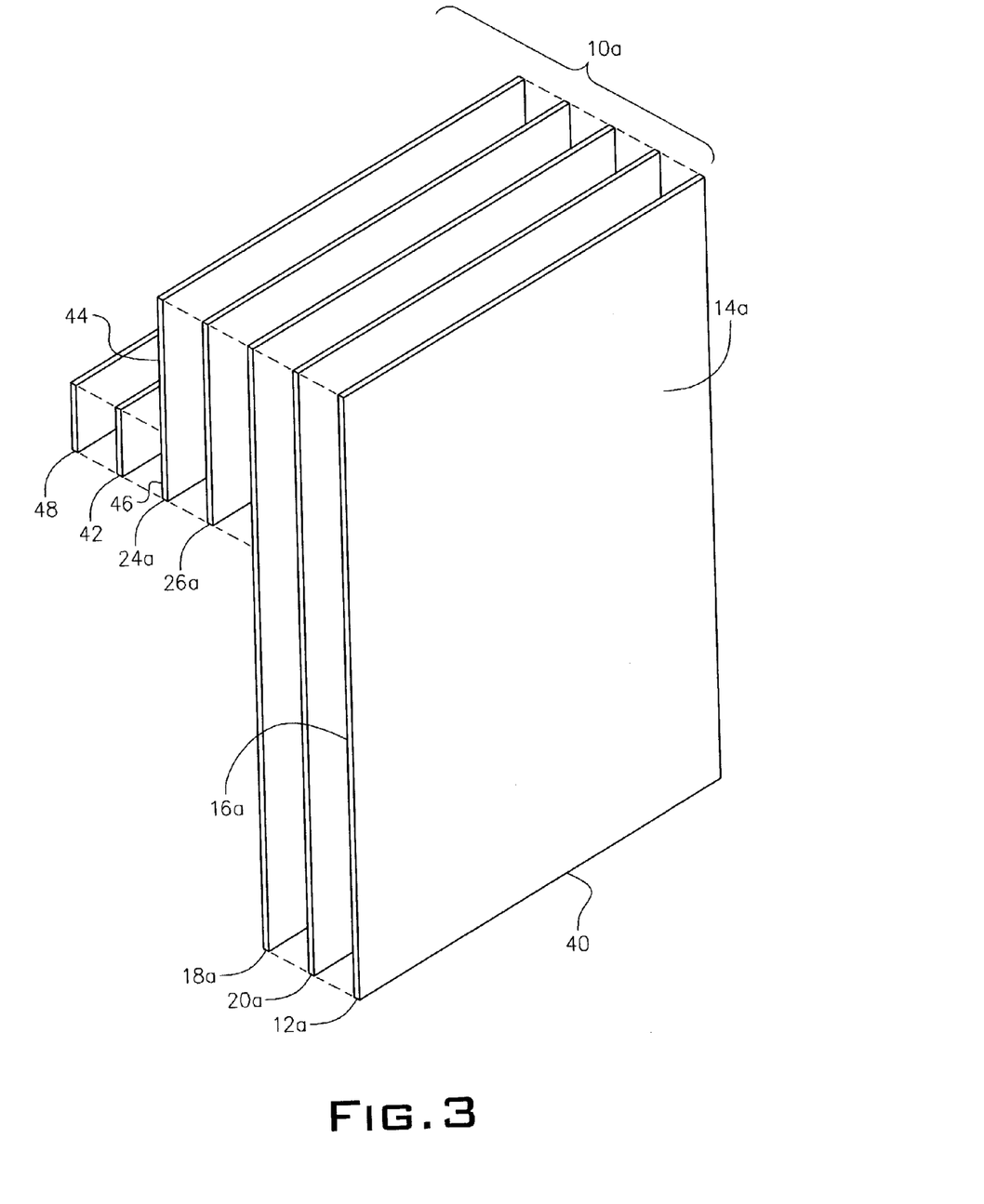
FIG. 3 is an exploded view of a first alternative card having seven layers.
Figure 4:
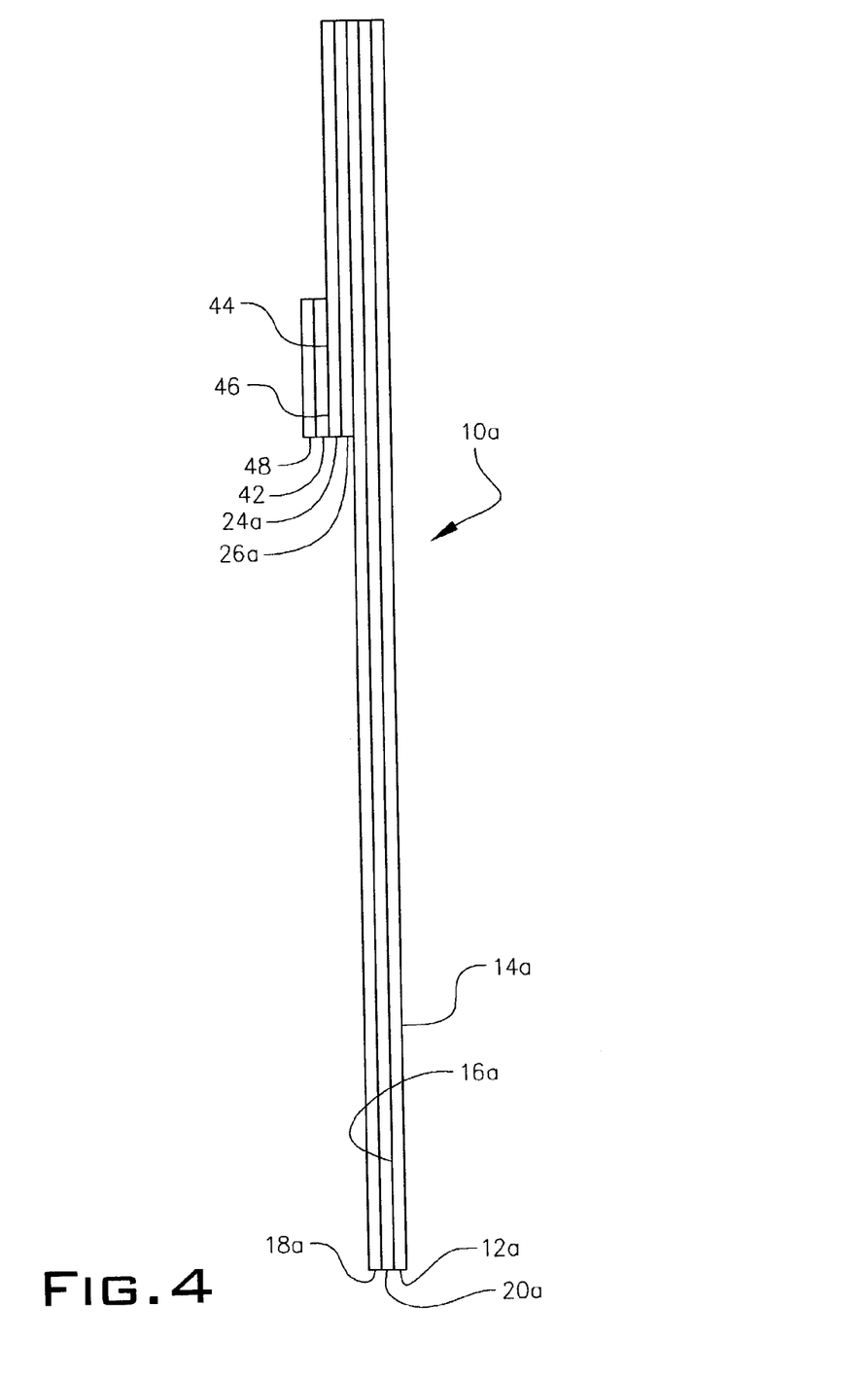
FIG. 4 is a side view of the seven layered card of FIG. 3.

A first alternative card 10a shown in FIGS. 3–4 has a first layer 12a of a printable, thin, flexible, non-moisture absorbable material such as polyvinyl chloride, polyester, cellophane or silver foil. A front surface 14a of first layer 12a contains indicia. A back surface 16a of first layer 12a is adhered to a six to ten point moisture absorbable card stock 18a by an intermediate high tack adhesive layer 20a. A flexible magnet sheeting 24a is adhered to the card stock 18a by an intermediate high tack adhesive layer 26a. A low tack adhesive layer 42 is applied to a back side 44 along a lower portion 46 of magnet 24a. A carrier layer 48 is adhered to the adhesive layer 42 until the adhesive layer 42 is needed for attaching card 10a to a vertical non-metal surface 38. The magnet alone can provide an attachment when surface 38 is a ferrous metal. A gauge 30 as shown in FIG. 1 and in FIGS. 9–11 can be separately made to indicate the curl of card 10a.

Figure 5:
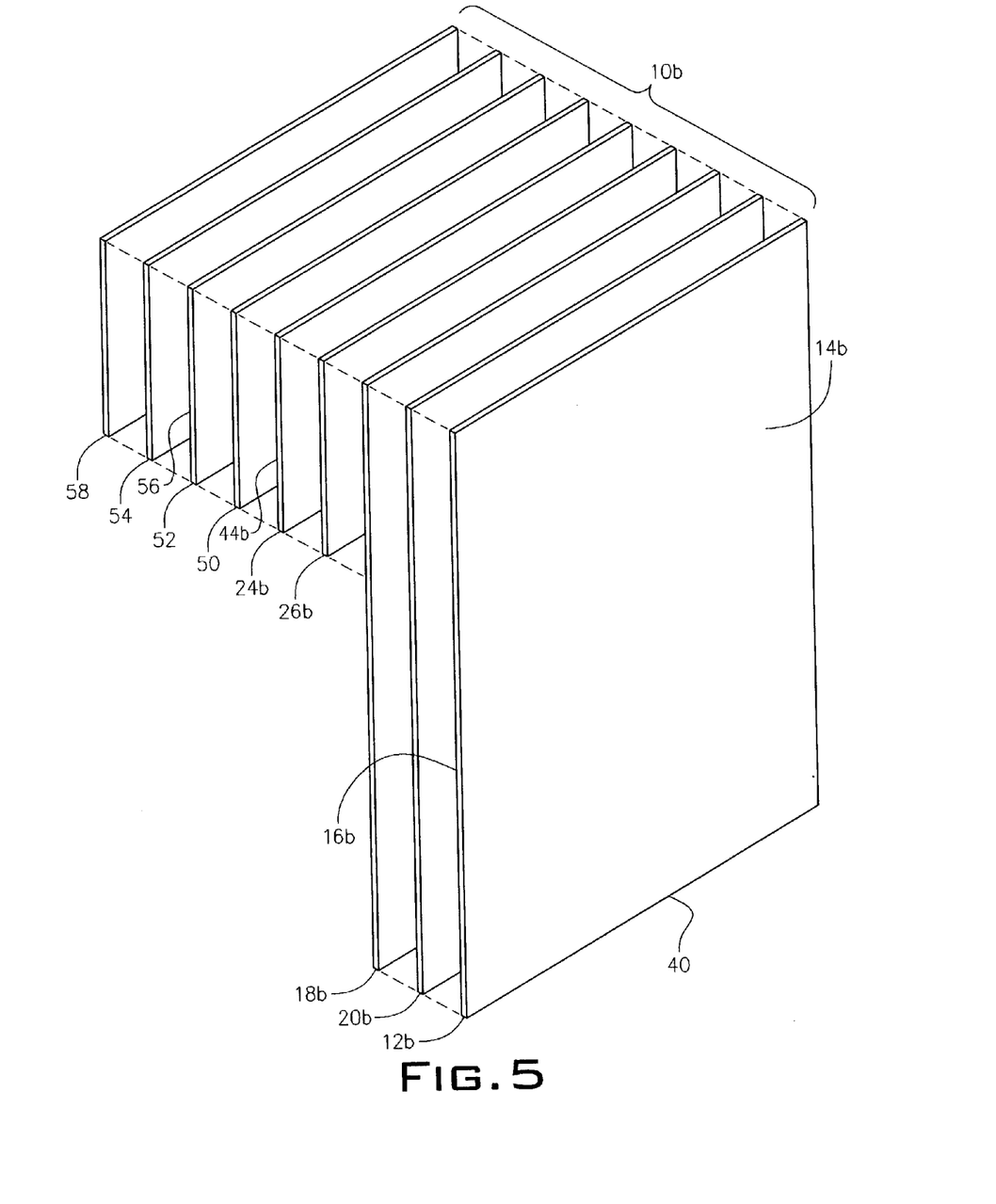
FIG. 5 is an exploded view of a second alternative card having nine layers.
Figure 6:
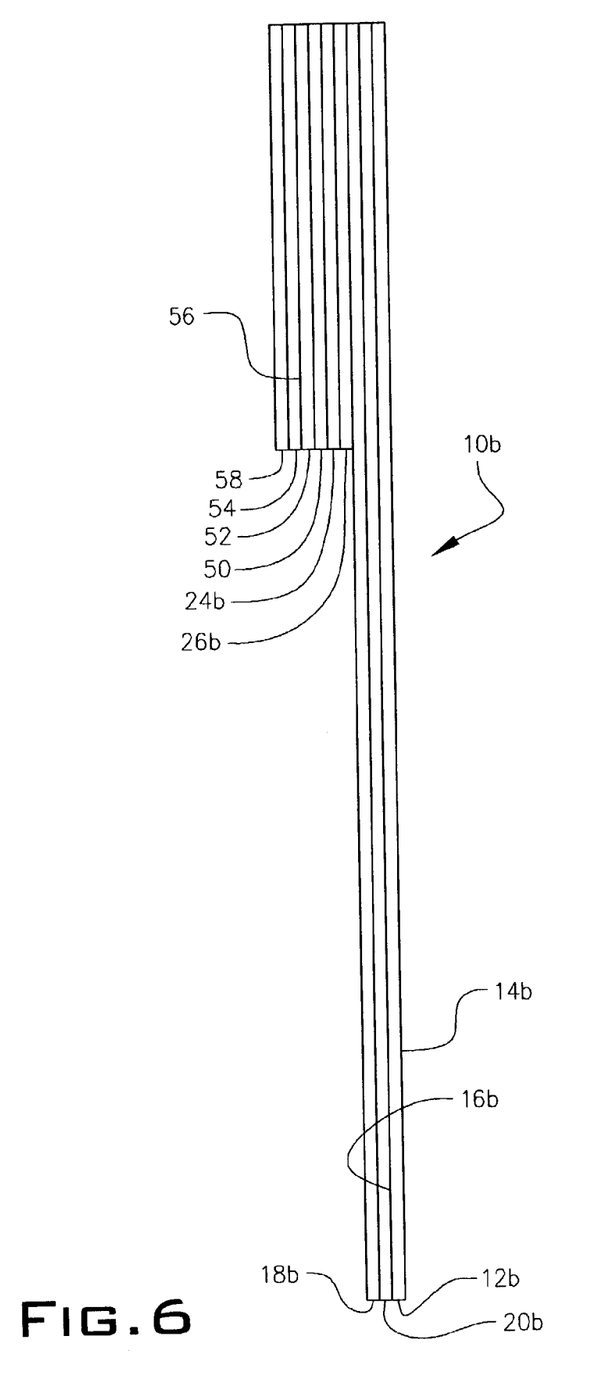
FIG. 6 is a side view of the nine layered card of FIG. 5.

A second alternative card 10b shown in FIGS. 5–6 has a first layer 12b of a printable, thin, flexible, non-moisture absorbable material such as polyvinyl chloride, polyester, cellophane or silver foil. A front surface 14b of first layer 12b contains indicia. A back surface 16b of first layer 12b is adhered to a six to ten point moisture absorbable card stock 18b by an intermediate high tack adhesive layer 20b. A flexible magnet sheeting 24b is adhered to the card stock 18b by an intermediate high tack adhesive layer 26a. A back side 44b of magnet 24b has a high tack layer 50 applied and a first carrier paper 52 over the layer 50. A low tack adhesive 54 is applied to a back side 56 of carrier paper 52 and a second carrier paper 58 is applied over the adhesive 54 for easy removal.

Figure 7:
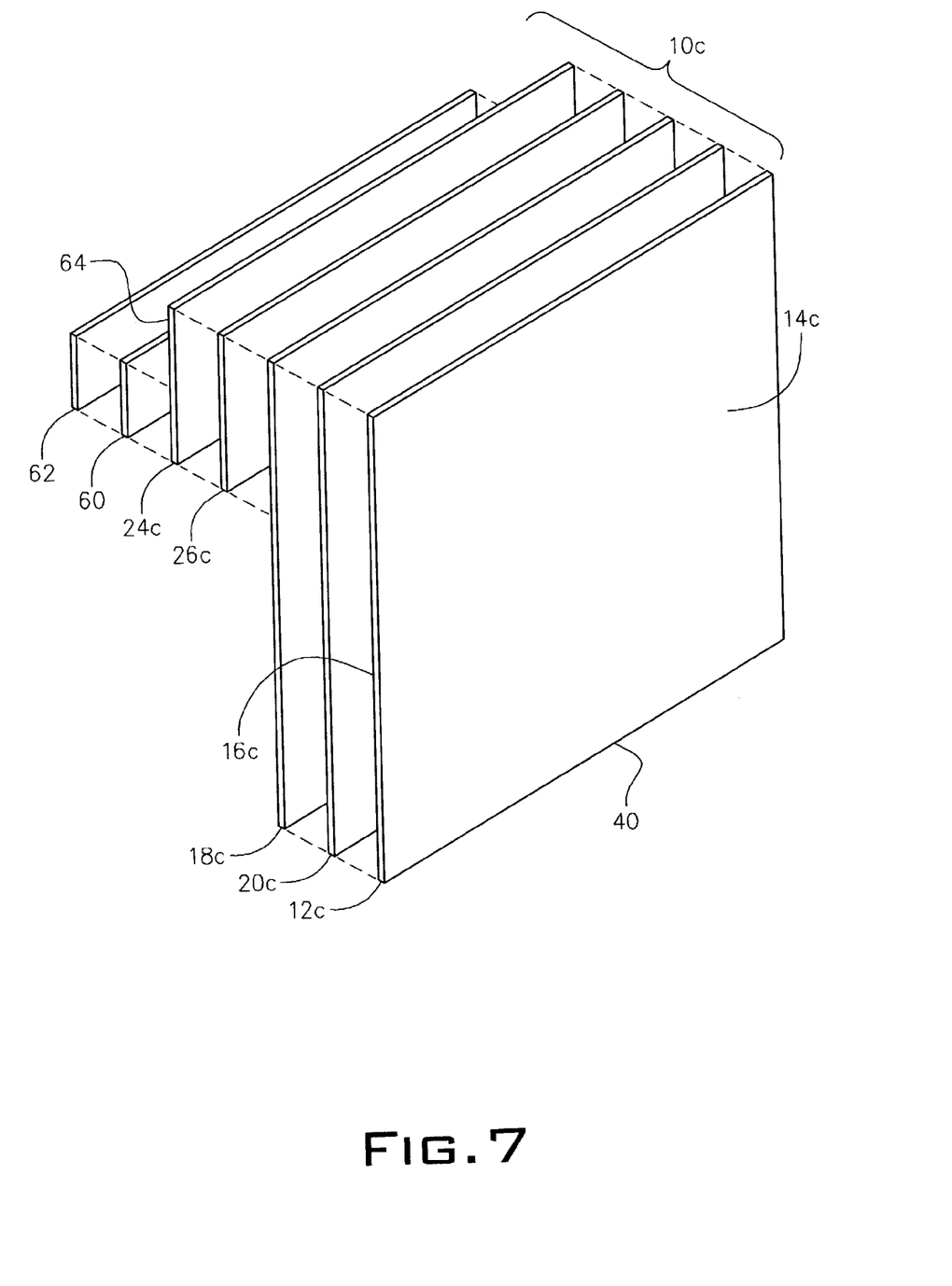
FIG. 7 is an exploded view of a square configuration third alternative card having seven layers.
Figure 8:
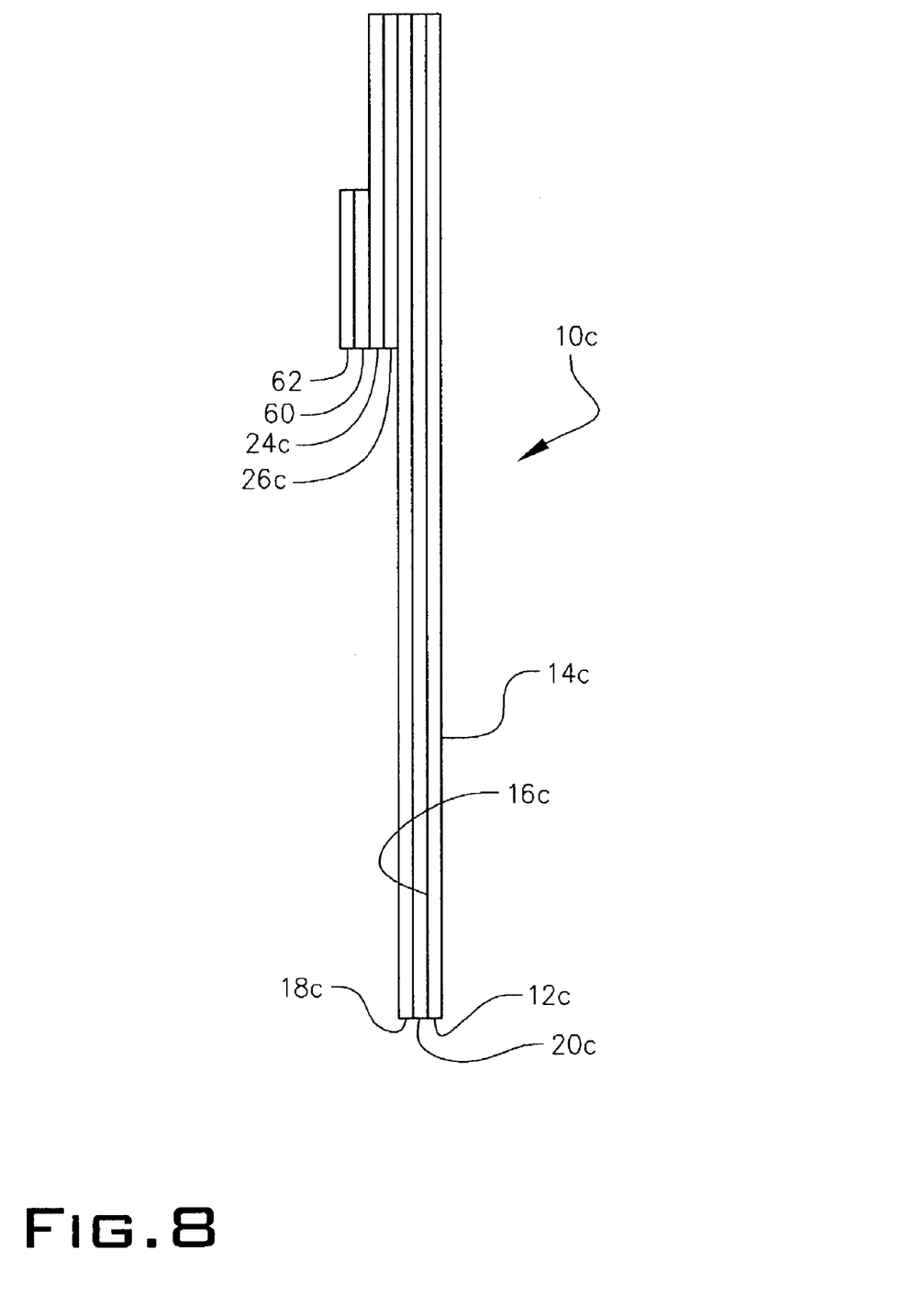
FIG. 8 is a side view of the third alternative card.

A third alternative card 10c shown in FIGS. 7–8 has a square configuration as compared to the rectangular card configuration of FIGS. 1–6. Card 10c has a first layer 12c of a printable, thin, flexible, non-moisture absorbable material such as polyvinyl chloride, polyester, cellophane or silver foil. A front surface 14c of first layer 12c contains indicia. A back surface 16c of first layer 12c is adhered to a six to ten point moisture absorbable card stock 18c by an intermediate high tack adhesive layer 20c. A flexible magnet sheeting 24c is adhered to the card stock 18c by a high tack adhesive layer 26c. A low tack adhesive 60 is attached to a back side 64 of magnet 24c. The low tack adhesive is covered by carrier paper 62 until the card 10c is ready for mounting on a vertical surface 38.

Although the alternative embodiments shown in FIGS. 3–8 do not show a perforation line and gauge as shown in FIGS. 1–2, such a gauge can be attached in the manner shown in FIG. 1 to a bottom edge 40. In the same manner, the embodiment shown in FIGS. 1–2 does not have to contain an attached gauge as the gauge can be separately created by a heavy grade of paper such as seen on business cards.

In all the cards 10, 10a, 10b and 10c, the card stock 18, 18a, 18b and 18c is a moisture absorbable paper. The first layer 12, adhesive layer 20 and card stock can be purchased from Fasson, Inc. The preferred first layer is silver foil obtained from Crown Roll Leaf. The high tack adhesive is a heat sensitive or pressure sensitive glue. The preferred card stock is about 8 point card stock. Preferably, the adhesive between the magnet sheet and card stock is a heat activated glue. The flexible magnet sheeting 24, 24a, 24b and 24c can be obtained from Flexmag Industries, Inc.

In use, gauge 30 along bottom line 40 is detached and the card 10, 10a, 10b or 10c, is exposed to ambient conditions in a room. As the card bottom line 40 curls upwardly as shown in FIGS. 9–11, the gauge 30 is held perpendicular to the mounting surface 38 and the moisture level is read from the gauge portions 32, 34, or 36.

Equivalent elements can be substituted for the elements shown to produce a card in the same way with the same function and same results.

Having disclosed the invention, what is claimed follows:

1. A device comprising a card and a gauge for measuring atmospheric humidity, the card containing multiple layers having a top and bottom horizontal edge and opposite vertical side edges, the card having:
    a first layer of a thin, flexible, non-moisture absorbable material, printable upon a front face;
    a second layer of a first high tack heat or pressure sensitive adhesive on a back side of the first layer;
    a third layer of a moisture absorbable card stock affixed to a back side of the flexible non-moisture absorbable material of the first layer by the high tack heat or pressure sensitive adhesive of the second layer;
    a flexible magnetic sheet layer affixed by a second high tack heat or pressure sensitive adhesive to an upper back side of the third layer; and
    the gauge for measuring atmospheric humidity attached to the card by a perforated edge;
    whereby upon exposure to atmospheric humidity and upon disengaging the gauge from the perforated edge of the card and placing the gauge substantially perpendicular to the card, the gauge is capable of measuring the atmospheric humidity by measuring the degree of curl produced by the humidity in the multiple layers of the bottom edge of the card.

2. The device according to claim 1, wherein the gauge is a section of the card depending from a bottom edge of the card along the perforated edge.

3. The device according to claim 2, wherein the gauge has three portions showing respectively, low humidity, normal humidity, and high humidity.

4. The device according to claim 1, wherein the opposite vertical side edges are longer than the top and bottom horizontal edges.

5. The device according to claim 1, wherein a portion of the flexible magnet sheet contains a low tack adhesive covered by a removable carrier material.

6. The device according to claim 1, wherein a back side of the flexible magnetic sheet is covered with a high tack adhesive and a front face of a first carrier material, a back side of the carrier material covered by a low tack adhesive and a second removable carrier material.

7. The device according to claim 1, wherein the moisture absorbable card stock layer is a 6 to 10 point grade.

8. The device according to claim 7, wherein the card stock layer is about an 8 point grade.

9. The device according to claim 1, wherein the thin, flexible, non-moisture absorbable material is a silver foil printable with a compatible water based ink.

10. A device comprising a card and a gauge for measuring atmospheric humidity, the card containing multiple layers having a top and bottom horizontal edge and opposite vertical side edges, the card having:
    a layer of a front face printable, thin, flexible, non-moisture absorbable material, adhering on a back side to a moisture absorbable card stock by a high tack heat or pressure sensitive adhesive;
    a flexible magnet sheet adhered to an upper back side of the moisture absorbable card stock by a high tack heat or pressure sensitive adhesive; and
    a gauge for determining ambient relative humidity attached to the bottom horizontal edge below a perforated edge of the card, the gauge having separate portions indicating low, normal and high humidity so that when detached from the card and placed perpendicular to a mounting surface supporting the card, the gauge interprets atmospheric humidity by measuring a curl in the bottom edge of the card.

11. The device according to claim 10, wherein the opposite vertical side edges are longer than the top and horizontal edges.

12. The device according to claim 10, wherein a portion of the flexible magnet sheet contains a low tack adhesive covered by a carrier material.

13. The device according to claim 10, wherein a back side of the flexible magnet sheet is covered with a high tack adhesive and a front face of a first carrier material, a back side of the carrier material covered by a low tack adhesive and a second removable carrier material.

14. The device according to claim 10, wherein the moisture absorbable card stock layer is a 6 to 10 point grade.

15. The device according to claim 10, wherein the thin, flexible, non-moisture absorbable material is silver foil.

16. The device according to claim 10, wherein the thin, flexible, non-moisture absorbable material is polyvinyl chloride.

17. The device according to claim 10, wherein the card stock layer is about an 8 point grade.

* * * * *